US00PP12520P2

(12) United States Plant Patent

Olesen et al.

(10) Patent No.: US PP12,520 P2

(45) Date of Patent: Apr. 2, 2002

(54) SHRUB ROSE PLANT NAMED 'POULRUST'

(76) Inventors: L. Pernille Olesen; Mogens N. Olesen, both of Hillerødvejen 49, DK-3480, Fredensborg (DK)

( * ) Notice: Subject to any disclaimer, the term of this patent is extended or adjusted under 35 U.S.C. 154(b) by 0 days.

(21) Appl. No.: 09/261,447

(22) Filed: Mar. 3, 1999

(51) Int. Cl.[7] ..... A01H 5/00

(52) U.S. Cl. ..... Plt./102

(58) Field of Search ..... Plt./102, 107, 123, Plt./141, 148, 149

(56) References Cited

PUBLICATIONS

UPOV–ROM, 2000/06, Plant Variety Database, GTI Jouve Retrieval Software, citation for 'Poulrest'.*

Copy of PL PBR Grant 000852, granted Feb. 22, 1999.*

Copy of DK PBR 16584, granted Dec. 12, 1996.*

Copy of NL PBR 17597, granted Nov. 11, 1997.*

Copy of EU 2037, granted Jun. 4, 1997 and EU 0592/95 filed Aug. 8, 1995.*

UPOV–ROM, 2000/04, Plant Variety Database GTI Jouve Retrieval Software, 3 citations for 'Poulrust'.*

* cited by examiner

*Primary Examiner*—Howard J. Locker

(57) ABSTRACT

A new garden rose plant which has abundant, semi-double, dark lavender pink flowers and attractive foliage. The plant grows well as a traditionally budded plant as well as from cuttings. This new and distinct variety has shown to be uniform and stable in the resulting generations from asexual propagation.

2 Drawing Sheets

SUMMARY OF THE INVENTION

The present invention constitutes a new and distinct variety of garden rose plant which originated from a controlled crossing between an unnamed seedling and Dorus Rijkers. The two parents were crossed during the summer of 1986, and the resulting seeds were planted in a controlled environment. The new variety is named 'POULrust'.

The new rose may be distinguished from its seed parent, an unnamed seedling, by the following combination of characteristics:

1. The seed parent is a low growing, spreading variety, while 'POULrust' is more upright.

2. The unnamed seedling has small, single, soft pink to white flowers.

The new variety may be distinguished from its pollen parent, Dorus Rijkers, by the following characteristic:

1. The pollen parent is a pink floribunda.

The objective of the hybridization of this rose variety for nursery and garden use was to create a new distinct variety with unique qualities, such as:

1. A garden rose plant with abundant, semi double, dark lavender pink flowers;

2. Abundant, shiny foliage on a vigorous yet compact growing plant;

3. Good growth as a traditionally budded plant as well as from cuttings.

4. Excellent disease resistance.

This combination of qualities is not present in previously available commercial cultivars of this type and distinguish 'POULrust' from all other varieties of which we are aware.

As part of their rose development program, L. Pernille Olesen and Mogens N. Olesen germinated the seeds from the aforementioned hybridization and conducted evaluations on the resulting seedlings in a controlled environment in Fredensborg, Denmark.

'POULrust' was selected by the inventors in the spring of 1987 as a single plant from the progeny of the aforementioned hybridization.

Asexual reproduction of 'POULrust' by traditional budding was first done by L. Pernille and Mogens N. Olesen in their nursery in Fredensborg, Denmark in August, 1987. This initial and other subsequent propagations conducted in controlled environments have demonstrated that the characteristics of 'POULrust' are true to type and are transmitted from one generation to the next.

BRIEF DESCRIPTION OF THE DRAWINGS

The accompanying color illustrations shows as true as is reasonably possible to obtain in color photographs of this type, the typical characteristics of the buds, flowers, leaves, stems, and a plant of 'POULrust'. Specifically illustrated in SHEET 1:

1. Stems showing branching and the attachment of leaves, buds, and peduncles;

2. Flower bud, partially opened bud, and open bloom;

3. Flower petals, detached;

Specifically illustrated in SHEET 2:

4. Sepals and pedicel;

5. Young stems;

6. Leaves;

7. Bare stems exhibiting thorns.

DETAILED DESCRIPTION OF THE VARIETY

The following is a description of 'POULrust', as observed in its outdoor growth in a field nursery in Jackson County, Oreg. Observations were conducted during August, 1998. Color references are made using The Royal Horticultural Society (London, England) Colour Chart, 1995, except where common terms of color are used.

For a comparison, several physical characteristics of the rose variety 'POULans', a shrub rose variety from the same inventors described and illustrated in U.S. Plant Pat. No. 9,664 and issued on Oct. 22, 1996 are compared to 'POULrust' in Chart 1.

CHART 1

| | 'POULrust' | 'POULans' |
|---|---|---|
| Flowers bud color, as sepals first divide. | Red–Purple Group 58B. | Red Group 53C. |
| Petalage, normal number of petals per flower. | 8–10 petals under normal conditions. | 18–26 petals under normal conditions |
| Number of flower buds borne per spray. | Multiple buds. Under normal conditions, 5–20 buds per stem. | Multiple buds. Under normal conditions, 3–9 buds per stem. |
| Plant size, height × width | 40–50 cm in height and 100 cm in width. | 90–120 cm in height and 90–120 cm in width. |

Parents:

*Seed parent.*—Unnamed, unpatented seedling.

*Pollen parent.*—Dorus Rijkers.

Classification:

*Botanical.*—*Rosa hybrida.*

*Commercial.*—Shrub rose variety.

FLOWER AND FLOWER BUD

Blooming habit: Continuous.

Flower bud:

*Size.*—Upon opening, 14 mm–20 mm in length from base of receptacle to end of bud.

*Bud form.*—Short, ovoid.

*Bud color.*—As sepals unfold, Red-Purple Group 58B. Red-Purple Group 67C at ¼ opening.

*Sepals.*—Green Group 143C. Weak foliaceous appendages on three of the five sepals. Surfaces of sepals moderately pubescent. Stipitate glands are abundant on the outerside and on the margins of the sepals.

*Receptacle.*—Surface: Generally smooth, although there are a limited number of stipitate glands on the surface. Shape: Pear shaped. Size: Small 4 mm(h)×4 mm(w). Color: Green Group 143C with intonations of Greyed-Red Group 183D on surfaces exposed to sunlight.

*Peduncle.*—Surface: Abundant stipitate glands. Length: 15 to 25 mm average length. Color: Green Group 143C. Pedicel has intonation of Greyed-Purple Group 183C. Strength: Upright.

*Borne.*—Generally multiple buds per stem, with 5–20 buds per flowering stem.

Flower bloom:

*Fragrance.*—Light to moderate wild rose scent.

*Duration.*—The blooms have a duration on the plant of 1 to 3 days. Each stem has numerous flowers opening in succession. As a cut flower, duration of 1 to 2 days. Petals fall cleanly away from plant.

Color:

*Size.*—Small. Average flower diameter is 30–50 mm when open.

*Form.*—Shape of flower when viewed from the side: Upon opening, upper part: Flattened convex. Upon opening, lower part: Convex. Open flower, upper part: Flat. Open flower, lower part: Concave.

*Petalage.*—Semi-double. Average range: 8–10 petals under normal conditions, with 0–3 petaloids.

*Upon opening, petals.*—Outermost petals: Upper Surface: Red-Purple Group 68A. Reverse Side: Red-Purple Group 68A. Innermost petals: Upper Surface: Red-Purple Group 68A. Reverse Side: Red-Purple Group 67C.

*Upon opening, basal petal spots.*—Outermost petals: Outer Side: Basal zone is Yellow Group 3B. Becoming Yellow Group 1D in the Middle Zone. Inner Side: Yellow Group 1C. Innermost petals: Outer Side: Yellow Group 12A. Inner Side: Yellow Group 12A.

*After opening, petals.*—Outermost petals: Upper Surface: Red-Purple Group 74D. Reverse Side: Red-Purple Group 74C. Innermost petals: Upper Surface: Red-Purple Group 66D. Reverse Side: Red-Purple Group 66D.

*After opening, basal petal spots.*—Outer Side: White group 155C. Inner Side: White Group 155C. Innermost petals: Outer Side: Green-White Group 157D. Inner Side: Green-White Group 157C.

General tonality: On open flower, Red-Purple Group 66D. No change in the general tonality of innermost petals at the end of the second day. Outermost petals fade to Red-Purple Group 66D by end of second day.

Petals:

*Petal reflex.*—Somewhat.

*Petal edge.*—Uniform.

*Shape.*—Deltoid shaped.

*Petaloids.*—Normally present. Quantity 0–3 petaloids.

*Thickness.*—Average.

*Arrangement.*—Informal.

Reproductive organs:

*Pollen.*—Color: Yellow-Orange Group 16A. Abundance: Limited.

*Anthers.*—Size: Small. Color: Greyed-Yellow Group 162B. Abundance: Average.

*Filaments.*—Color: Yellow-Orange Group 17B. Abundance: Average.

*Stigmas.*—Inferior in location to anthers. Color: Greyed-Yellow Group 162D.

*Styles.*—Color: Red-Purple Group 61B.

*Hips.*—None observed.

PLANT

Plant growth: Moderately vigorous. When grown as a field grown nursery plant, either on its own roots or budded on *R. multiflora* root stock, the average height of the plant itself is 40–50 cm and the average width is 100 cm.

Stems:

*Color.*—Young wood: Green Group 143B. New stems often with intonations of Greyed-Purple Group 183C. Older wood: Green Group 143C.

*Thorns.*—Incidence: Older wood has few thorns. Young wood has many fine prickles. Size: Average length: 1 mm–4 mm. Color: Variable. From Green Group 143C to Greyed-Orange Group 164B–166A. Shape: Concave.

*Surface*.—Young wood: Rough. Older wood: Smooth.

Plant foliage: Normal number of leaflets on normal leaves in middle of the stem: 7 leaflets.

*Leaf size—Medium,* 120 mm (l)×75 mm (w).

*Abundance*.—Average.

*Color*.—Upper Leaf Surface: Green Group 137A. Lower Leaf Surface: Green Group 137C. Juvenile foliage: Upper Surface: Green Group 143A–144A. Lower Surface: Green Group 137A. No anthocyanin coloration observed.

Plant leaves and leaflets:

*Stipules*.—Present. Abundant numbers of stipitate glands present. Size: 15 mm (l)–5 mm (w). Color: Yellow-Green Group 144A.

*Petiole*.—Length: 20 mm average. Color: Yellow-Green Group 144A. Underneath: Prickles present. Margins: Stipitate hairs present.

*Rachis*.—Color: Yellow-Green Group 144A. Underneath: Prickles present. Margins: Stipitate glands present.

*Leaflet*.—Edge: Finely serrated. Shape: Elliptic. Texture: Moderately glossy.

Disease resistance: Excellent resistance to mildew, Black spot, and Botrytis under normal growing conditions in Jackson County, Oreg.

Winter hardiness: Winter hardy in Denmark and in Jackson County, Oreg.

We claim:

1. A new and distinct variety of garden rose plant of the shrub class, substantially as herein illustrated and described as a distinct and novel rose variety due to its abundant, semi-double, dark lavender pink flowers, extended period of bloom; shiny foliage on a vigorous yet compact growing plant; good growth as a traditionally budded plant as well as from cuttings; and excellent disease resistance.

* * * * *

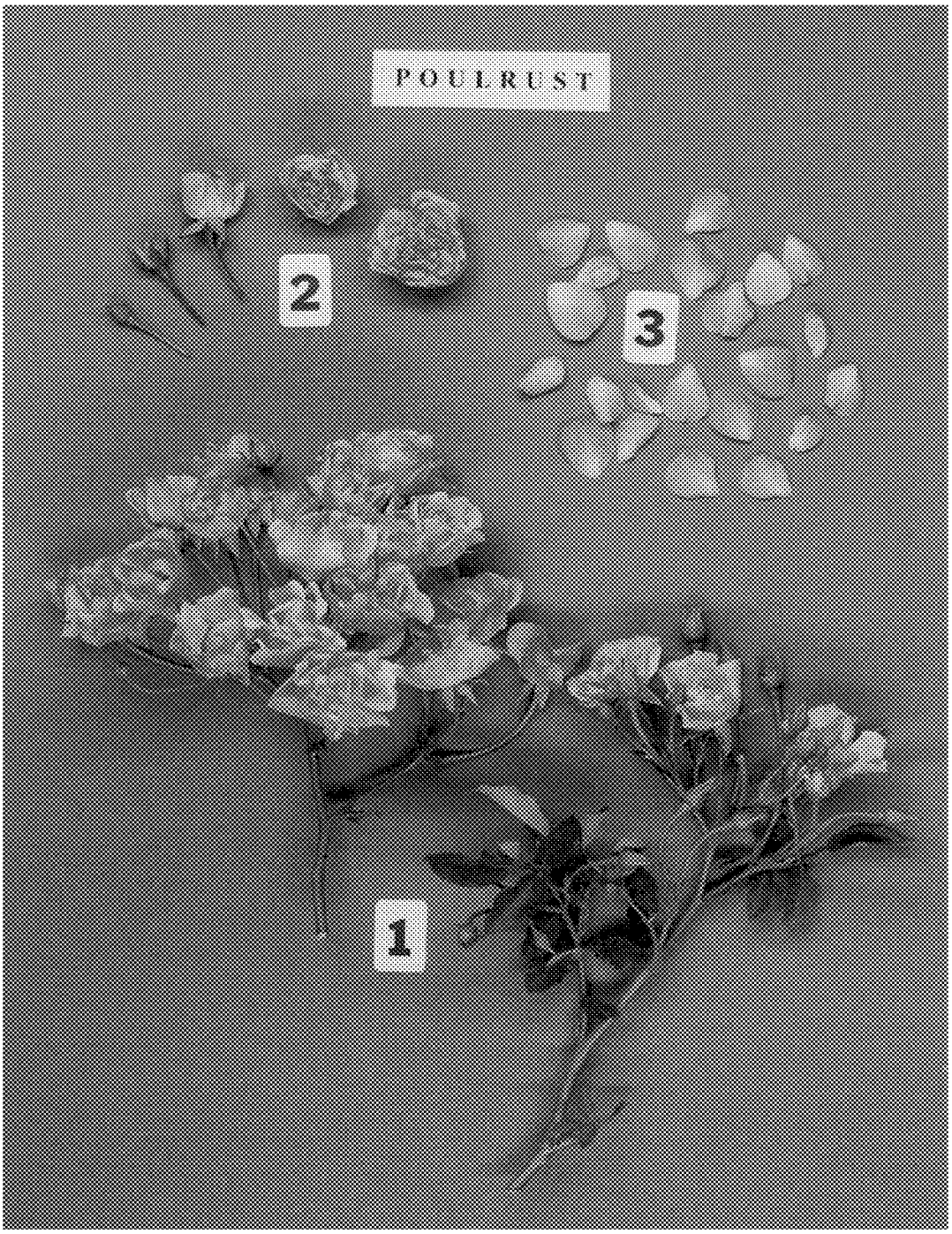
POULRUST
2
3
1

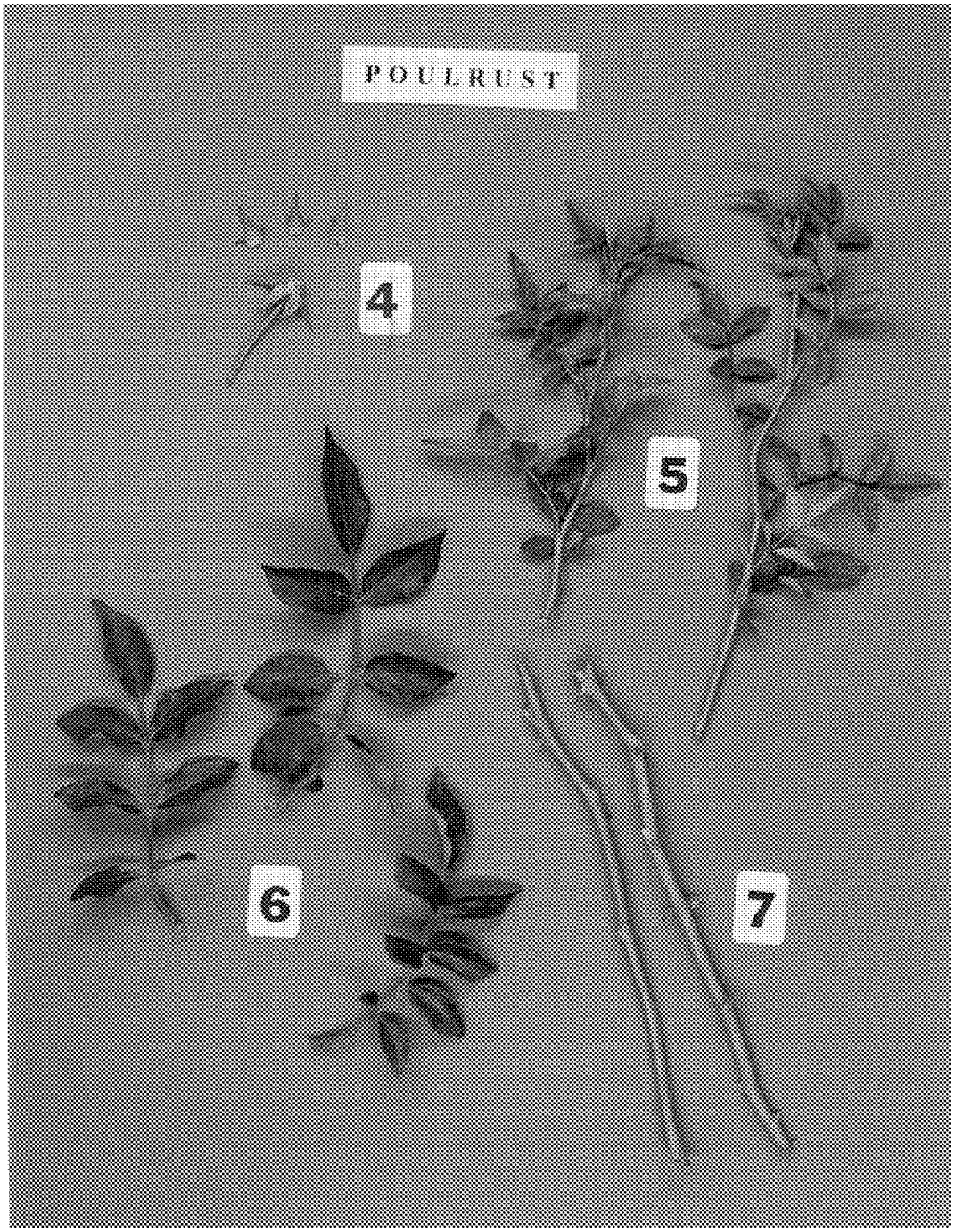
POULRUST
4
5
6
7